United States Patent
Tanaka et al.

(10) Patent No.: US 10,925,813 B2
(45) Date of Patent: Feb. 23, 2021

(54) SUNSCREEN COMPOSITION

(71) Applicant: OTSUKA PHARMACEUTICAL CO., LTD., Tokyo (JP)

(72) Inventors: Masahiko Tanaka, Osaka (JP); Miyoko Ogihara, Osaka (JP); Junko Kako, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/383,010

(22) PCT Filed: Jan. 25, 2013

(86) PCT No.: PCT/JP2013/051651
§ 371 (c)(1),
(2) Date: Sep. 4, 2014

(87) PCT Pub. No.: WO2013/132914
PCT Pub. Date: Sep. 12, 2013

(65) Prior Publication Data
US 2015/0216766 A1  Aug. 6, 2015

(30) Foreign Application Priority Data

Mar. 5, 2012  (JP) .................................. 2012-048258
Jul. 13, 2012  (JP) .................................. 2012-158118

(51) Int. Cl.
A61K 8/02 (2006.01)
A61K 8/895 (2006.01)
(Continued)

(52) U.S. Cl.
CPC ............ A61K 8/025 (2013.01); A61K 8/0241 (2013.01); A61K 8/064 (2013.01); A61K 8/34 (2013.01); A61K 8/41 (2013.01); A61K 8/585 (2013.01); A61K 8/606 (2013.01); A61K 8/676 (2013.01); A61K 8/89 (2013.01); A61K 8/895 (2013.01);
(Continued)

(58) Field of Classification Search
CPC ......... A61K 8/064; A61K 8/895; A61Q 17/04
See application file for complete search history.

(56) References Cited

U.S. PATENT DOCUMENTS 4,698,178 A * 10/1987 Huttinger ................. A61K 8/06
106/287.14
5,663,213 A   9/1997 Jones et al.
(Continued)

FOREIGN PATENT DOCUMENTS

JP  H 09-104822 A   4/1997
JP  2003-286125 A  10/2003
(Continued)

OTHER PUBLICATIONS

English Machine Translation of JP 2007-269690; Accessed May 6, 2015.*
(Continued)

*Primary Examiner* — Bethany P Barham
(74) *Attorney, Agent, or Firm* — Finnegan, Henderson, Farabow, Garrett & Dunner LLP

(57) ABSTRACT

The present invention provides a sunscreen composition comprising two or more oil-soluble ultraviolet absorbers and composite silicone particles having an average particle diameter of 10 μm or less.

4 Claims, 1 Drawing Sheet

(51) Int. Cl.
  A61K 8/06    (2006.01)
  A61K 8/58    (2006.01)
  A61K 8/67    (2006.01)
  A61K 8/89    (2006.01)
  A61Q 17/04   (2006.01)
  A61K 8/60    (2006.01)
  A61K 8/34    (2006.01)
  A61K 8/41    (2006.01)

(52) U.S. Cl.
  CPC ........ *A61Q 17/04* (2013.01); *A61K 2800/412* (2013.01); *A61K 2800/5922* (2013.01); *A61K 2800/624* (2013.01)

(56) References Cited

U.S. PATENT DOCUMENTS

| | | | |
|---|---|---|---|
| 5,837,697 A * | 11/1998 | Blank et al. ................ | 514/159 |
| 2007/0173599 A1 * | 7/2007 | Liu .......................... | A61K 8/06 524/588 |
| 2008/0081024 A1 * | 4/2008 | Beasley ................... | A61K 8/37 424/59 |
| 2009/0074822 A1 | 3/2009 | Declercq et al. | |
| 2010/0233103 A1 | 9/2010 | Shirao et al. | |
| 2010/0292509 A1 | 11/2010 | Kajiya et al. | |
| 2011/0112045 A1 * | 5/2011 | Wakamatsu ........... | A61K 8/342 514/47 |
| 2013/0011348 A1 | 1/2013 | Takakura | |

FOREIGN PATENT DOCUMENTS

| | | |
|---|---|---|
| JP | 2005/325088 A | 11/2005 |
| JP | 2007-161650 A | 6/2007 |
| JP | 2007-246521 A | 9/2007 |
| JP | 2007-269690 A | 10/2007 |
| JP | 2008-001643 A | 1/2008 |
| JP | 2008-001644 | 1/2008 |
| JP | 2008/189609 A | 8/2008 |
| JP | 2008-273880 A | 11/2008 |
| JP | 2009-524644 A | 7/2009 |
| JP | 2009-209139 | 9/2009 |
| JP | 2009-235046 | 10/2009 |
| JP | 2010-184912 A | 8/2010 |
| JP | 2011-157282 A | 8/2011 |
| KR | 10-2009-0006128 A | 1/2009 |
| WO | WO 2007/086022 A2 | 8/2007 |
| WO | WO 2007/133769 A2 | 11/2007 |
| WO | WO2009/067095 * | 5/2009 ............... A61K 9/00 |
| WO | WO 2009/093534 A1 | 7/2009 |
| WO | WO 2010/147238 A1 | 12/2010 |
| WO | WO 2012/026325 A1 | 3/2012 |

OTHER PUBLICATIONS

Seii Kyo, "Silica Nano Ryushi o Mochiita Emulsion Nyuka Tokusei", Fragrance Journal, Apr. 26, 2005, No. 19, pp. 39-44.
English-language translation of the International Search Report from the Japanese Patent Office in corresponding International Application No. PCT/JP2013/051651 dated Apr. 23, 2013.
Seii Kyo, "Silica Nano Ryushi o Mochiita Emulsion Nyuka Tokusei", Frangrance Journal, Apr. 26, 2005, No. 19, pp. 39-44.
Shin-Etsu Silicones for Personal Care Product Brochure KSP Series, 2004, 2-3.
Office Action dated Nov. 22, 2016, for the corresponding Japanese patent application No. 2014-503712.
Sun Block for Face & Body, ID1088664, Mintel GNPD online, Mar. 2009.
Anti-Ageing Sun Lotion for Face SPF30, ID762432, Mintel GNPD online, Aug. 2007.
Anti-Ageing Sun Lotion for Body, ID803406, Mintel GNPD online, Nov. 2007.
Decision of Refusal dated May 23, 2017 for corresponding JP Patent Application No. 2014-503712.
Office Action for corresponding KR Application No. KR 10-2014-7027569 dated Feb. 13, 2018.
"Effect of Salt Type on the Emulsifying Properties of Water-in-oil Emulsions Prepared with Diacylglycerol Without an Emulsifier," Bulletin of the Graduate School of Human Life Sciences, Showa Women's University, 2005, vol. 14, pp. 31-38.
The Chemical Society of Japan, 1989, vol. 10, pp. 1693-1699.
Blog posted on http://tangerinetotty.pixnet.net/blog/post/26845433 (2010).
News Release on SHISEIDO Web Site (http://ww.shiseidogroup.jp/newsimg/archive/00000000001106/1106_w6y10_jp.pdf) on Jan. 20, 2010.
Office Action dated Oct. 4, 2018 by the Japanese Patent Office in counterpart Japanese Patent Application No. 2017-159666.
Perfect Essence Sunscreen, ID1290692, Minel GNPD, Mar. 2010.
Database GNPD [Online] Mintel; "Super Plus Beblesh Balm", Feb. 1, 2010, Database Accession No. 1261508.
Extended European Search Report for corresponding EP Application No. 13758285.4 dated Oct. 16, 2015.

* cited by examiner

SUNSCREEN COMPOSITION

CROSS REFERENCE TO RELATED PATENT APPLICATIONS

The present application is the national phase of International Application No. PCT/JP20131051651, titled "SUNSCREEN COMPOSITION", filed on Jan. 25, 2013, which claims the priority of Japanese Patent Application No. 2012-048258, filed with the Japanese Patent Office on Mar. 5, 2012, and Japanese Patent Application No. 2012-158118, filed with the Japanese Patent Office on Jul. 13, 2012, all of which applications are incorporated herein in their entireties by reference.

TECHNICAL FIELD

The present invention relates to a sunscreen composition having an excellent ultraviolet protection effect. Moreover, the present invention relates to a sunscreen composition that is stable and gentle to the skin, and that has excellent water resistance and a high ultraviolet protection effect.

BACKGROUND ART

Conventionally, sunscreen agents are often used to protect the skin from ultraviolet radiation. In recent years, sunscreen cosmetics tend to be used regardless of season, sex, and age, and demand for sunscreen cosmetics is still increasing at present.

The ultraviolet protection performance of a sunscreen agent can be represented by SPF (sun protection factor), which shows the protection index of UV-B (wavelength: 290 to 320 nm), PFA (protection factor of UVA), which shows the protection index of UV-A (wavelength: 320 to 400 nm), or PA (protection grade of UVA), which is the classification indication based on PFA. The higher the SPF value and/or the PFA value are, the higher the ultraviolet protection performance is supposed to be. Sunscreen agents with SPF values and/or PFA values are generally intended for use in daily life, such as when staying indoors and when going out for a short period of time. Among them, sunscreen agents with high SPF values and/or high PFA values are intended for use in places exposed to high doses of ultraviolet radiation, such as places where long-term outdoor activities and outdoor sports (e.g., sea, mountain, and ski areas) are enjoyed.

Many sunscreen agents have been reported so far. For example, PTL 1 discloses an oil-in-water type sunscreen agent having an average emulsified particle size of 700 nm or less and comprising octyl methoxycinnamate, t-butyl methoxydibenzoyl methane and/or 2-hydroxy-4-methoxybenzophenone, a specific polyoxyethylene-polyoxyalkylene alkyl ether block polymer, and a nonpolar oil in specific proportions. The oil-in-water type sunscreen agent disclosed in PTL 1 has a high ultraviolet absorber content to thereby enhance ultraviolet protection ability, and has excellent emulsion stability and good usability. Further, PTL 2 discloses an ultraviolet absorbing composition comprising specific latex particles and an ultraviolet absorber, the ultraviolet absorbing composition having a higher ultraviolet absorbing effect than a composition that does not contain latex particles.

As described above, many sunscreen agents have already been reported and sold. However, these days, an increased amount of ultraviolet radiation reaches the Earth's surface due to the impact of the depletion of the ozone layer, etc.; accordingly, demand for sunscreen agents having a high ultraviolet protection effect has still been increasing. Furthermore, stable sunscreen agents that are gentle to the skin while having a high ultraviolet protection effect are expected to further increase consumers' sense of security and satisfaction.

CITATION LIST

Patent Literature

PTL 1: JP2011-157282A
PTL 2: JPH09-104822A

SUMMARY OF INVENTION

Technical Problem

From the viewpoint of enhancing the ultraviolet protection effect, it is considered important to impart a high ultraviolet protection effect to sunscreen agents. Moreover, the reduction of the ultraviolet protection effect of a sunscreen agent over time can be prevented by further imparting strong water resistance against sweat and water to the sunscreen agent. Accordingly, an object of the present invention is to provide a sunscreen composition that has a superior sunscreen effect. Another object of the present invention is to provide a sunscreen composition that is stable and gentle to the skin, and that has a high sunscreen effect and excellent water resistance.

Solution to Problem

As a result of extensive research to achieve the above objects, the present inventors found that the SPF value of a sunscreen composition can be improved by incorporating therein two or more oil-soluble ultraviolet absorbers and composite silicone particles having an average particle diameter of 10 µm or less. Further, the present inventors found that this composition also has excellent water resistance. Moreover, the present inventors found that a sunscreen composition with a desired high PFA value can be thereby obtained. Furthermore, the present inventors found that a sunscreen composition with a higher PFA value can be obtained by using, in particular, three or more oil-soluble ultraviolet absorbers. The present invention has been accomplished upon further studies on the stability based on these findings.

More specifically, the present invention provides the following inventions:

Item 1. A sunscreen composition comprising two or more oil-soluble ultraviolet absorbers and composite silicone particles having an average particle diameter of 10 µm or less.
Item 2. The sunscreen composition according to item 1, wherein the oil-soluble ultraviolet absorbers are at least two members selected from the group consisting of ethylhexyl methoxycinnamate, octocrylene, diethylamino hydroxybenzoyl hexyl benzoate, polysilicone-based ultraviolet absorbers, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramnethylbutylphenol, oxybenzone-3, and drometrizole trisiloxane.
Item 3. The sunscreen composition according to item 1 or 2, wherein the oil-soluble ultraviolet absorbers are at least two members selected from the group consisting of ethylhexyl methoxycinnamate, octocrylene, diethylamino hydroxybenzoyl hexyl benzoate, and polysilicone-15.

Item 4. The sunscreen composition according to any one of items 1 to 3, which has an SPF value of 50 or more as an indicator of UV-B protection ability.

Item 5. The sunscreen composition according to any one of items 1 to 4, which comprises three or more oil-soluble ultraviolet absorbers.

Item 6. The sunscreen composition according to any one of items 1 to 5, wherein the oil-soluble ultraviolet absorbers are diethylamino hydroxybenzoyl hexyl benzoate and at least two members selected from the group consisting of ethylhexyl methoxycinnamate, octocrylene, polysilicone-based ultraviolet absorbers, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramethylbutylphenol, oxybenzone-3, and drometrizole trisiloxane.

Item 7. The sunscreen composition according to any one of items 1 to 6, which has a PFA value of 5 or more as an indicator of UV-A protection ability.

Item 8. The sunscreen composition according to any one of items 1 to 7, wherein the oil-soluble ultraviolet absorbers comprise ethylhexyl methoxycinnamate, octocrylene, diethylamino hydroxybenzoyl hexyl benzoate, and polysilicone-15.

Item 9. The sunscreen composition according to any one of items 1 to 8, wherein the composite silicone particles are composite silicone particles in which silicone rubber is coated with a silicone resin.

Item 10. The sunscreen composition according to any one of items 1 to 9, wherein the composite silicone particles are composite silicone particles in which spherical silicone rubber is coated with a silicone resin.

Item 11. The sunscreen composition according to any one of items 1 to 10, wherein the composite silicone particles have an average particle diameter of 2 μm to 10 μm.

Item 12. The sunscreen composition according to any one of items 1 to 11, wherein the oil-soluble ultraviolet absorbers are contained in a total amount of 10 wt. % or more.

Item 13. The sunscreen composition according to any one of items 1 to 12, wherein the composite silicone particles are contained in an amount of 4 to 20 wt. %.

Item 14. The sunscreen composition according to any one of items 1 to 13, which is in the form of a water-in-oil type (W/O) emulsion.

Item 15. The sunscreen composition according to any one of items 1 to 14, further comprising at least one electrolyte selected from the group consisting of inorganic salts, purine-based compounds, and water-soluble vitamins, water-soluble vitamin derivatives, and salts thereof.

Item 16. The sunscreen composition according to item 15, wherein the electrolyte is at least one member selected from the group consisting of inorganic chloride, inorganic sulfide, and adenosine phosphate, ascorbic acid, ascorbic acid derivatives, and salts thereof.

Item 17. The sunscreen composition according to item 15 or 16, wherein the electrolyte is at least one member selected from the group consisting of chloride and/or sulfide of sodium, magnesium, or calcium, and adenosine monophosphate, ascorbic acid, ascorbic acid derivatives, and salts thereof.

Item 18. The sunscreen composition according to any one of items 15 to 17, wherein the electrolyte is a combination of at least one member selected from the group consisting of chloride and/or sulfide of sodium, magnesium, or calcium, and at least one member selected from the group consisting of adenosine monophosphate, ascorbic acid, ascorbic acid derivatives, and salts thereof.

Item 19. The sunscreen composition according to any one of items 15 to 18, wherein the electrolyte comprises adenosine monophosphate or a salt thereof, and at least one member selected from the group consisting of chloride and/or sulfide of sodium, magnesium, or calcium, and further comprises an essential oil.

Item 20. The sunscreen composition according to any one of items 15 to 19, wherein the electrolyte is contained in an amount of 0.5 wt. % or more.

Item 21. The sunscreen composition according to any one of items 1 to 20, wherein 10 to 40 wt. % of water is contained in the sunscreen composition.

Item 22. The sunscreen composition according to any one of items 15 to 21, wherein the electrolyte is contained in an amount of 1.5 to 40 parts by weight, based on 100 parts by weight of water.

Item 23. The sunscreen composition according to any one of items 1 to 22, which has a viscosity at 20° C. of 100 to 1,000 mPa·s.

Item 24. The sunscreen composition according to any one of items 1 to 23, which is free from an ultraviolet scattering agent.

Item 25. The sunscreen composition according to item 24, wherein the ultraviolet scattering agent is a metal oxide.

Item 26. Use of two or more oil-soluble ultraviolet absorbers and composite silicone particles having an average particle diameter of 10 μm or less for producing a sunscreen composition.

Item 27. The use according to item 26, wherein the sunscreen composition, the oil-soluble ultraviolet absorbers, and/or the composite silicone particle having an average particle diameter of 10 μm or less have the feature defined in at least any of items 1 to 25.

Item 28. Use of two or more oil-soluble ultraviolet absorbers and composite silicone particles having an average particle diameter of 10 μm or less for improving an ultraviolet protection effect of a sunscreen composition.

Item 29. The use according to item 28, wherein the sunscreen composition, the oil-soluble ultraviolet absorbers, and/or the composite silicone particle having an average particle diameter of 10 m or less have the feature defined in at least any of items 1 to 25.

Item 30. A method for improving an ultraviolet protection effect of a sunscreen composition comprising oil-soluble ultraviolet absorbers, the method using two or more oil-soluble ultraviolet absorbers and composite silicone particles having an average particle diameter of 10 μm or less.

Item 31. The method according to item 30, wherein the sunscreen composition, the oil-soluble ultraviolet absorbers, and/or the composite silicone particle having an average particle diameter of 10 μm or less have the feature defined in at least any of items 1 to 25.

Advantageous Effects of Invention

The sunscreen composition of the present invention has higher ultraviolet protection ability than that of conventional ultraviolet absorbers. Moreover, when the sunscreen composition of the present invention is formed into a water-in-oil (W/O) type emulsion, the sunscreen composition particularly has water resistance against, sweat, water, etc. Accordingly, the sunscreen composition of the present invention in the form of a water-in-oil type emulsion has excellent effects in that the desired ultraviolet protection effect can last for a long period of time, and that the sunscreen composition is much less likely to be removed from the skin due to sweat, water, etc. Therefore, the sunscreen composition of the present invention is not only useful for use in daily life, such as when staying indoors and when going out for a short period of time, but also useful in places exposed to high doses of ultraviolet radiation, such as places where long-term outdoor activities and outdoor sports are enjoyed, for which an even higher ultraviolet protection effect is required.

In spite of the above excellent effects and high resistance to water and sweat, the sunscreen composition of the present invention further has an advantage such that the skin is less likely to be whitened when the sunscreen composition is applied. Furthermore, the sunscreen composition of the present invention is easily washed off, and has significantly improved usability. In addition, when the sunscreen composition of the present invention further comprises an electrolyte, particularly when the sunscreen composition in the form of a water-in-oil type emulsion comprises a specific amount of electrolyte, a high sunscreen effect and water resistance are exhibited, and the water-in-oil type emulsion form can be maintained in an excellent state for a long period of time. This makes the sunscreen composition of the present invention more excellent in terms of stability over time.

DESCRIPTION OF EMBODIMENTS

Figure 1:
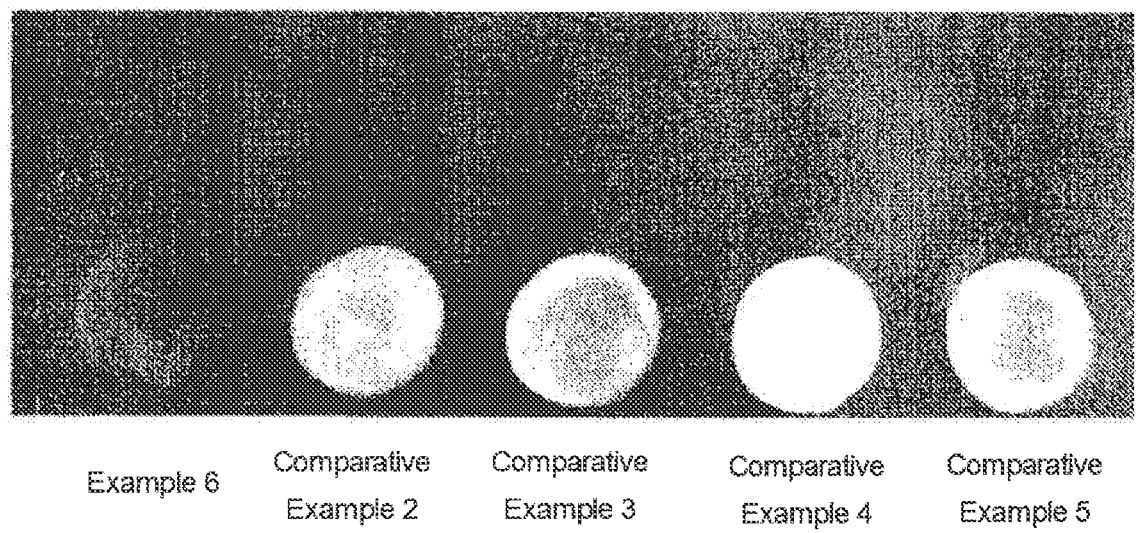
FIG. 1 is a photograph showing the results of the evaluation of the degree of whitening.

The sunscreen composition of the present invention is described below.

The sunscreen composition of the present invention comprises two or more oil-soluble ultraviolet absorbers and composite silicone particles having an average particle diameter of 10 μm or less.

Oil-soluble ultraviolet absorbers are not limited as long as they are soluble in oil and have the capability of absorbing ultraviolet radiation. Various oil-soluble ultraviolet absorbers can be used, regardless of whether they are in the form of a solid, semi-solid, or liquid. Examples of oil-soluble ultraviolet absorbers include ethylhexyl methoxycinnamate, octocrylene, diethylamino hydroxybenzoyl hexyl benzoate, polysilicone-based ultraviolet absorbers, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramethylbutylphenol, oxybenzone-3, ethylhexyl dimethyl PABA, drometrizole trisiloxane, and the like. Preferred among these oil-soluble ultraviolet absorbers are ethylhexyl methoxycinnamate, octocrylene, diethylamino hydroxybenzoyl hexyl benzoate, polysilicone-based ultraviolet absorbers, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramethylbutylphenol, oxybenzone-3, and drometrizole trisiloxane; more preferred are ethylhexyl methoxycinnamate, octocrylene, diethylamino hydroxybenzoyl hexyl benzoate, polysilicone-based ultraviolet absorbers, homosalate, t-butyl methoxybenzoyl methane, ethylhexyl salicylate, ethylhexyl triazone, bis-ethylhexyloxyphenol methoxyphenyl triazine, and methylene-bis-benzotriazolyl tetramethylbutylphenol; and still more preferred are ethylhexyl methoxycinnamate, octocrylene, diethylamino hydroxybenzoyl hexyl benzoate, and polysilicone-based ultraviolet absorbers. Examples of polysilicone-based ultraviolet absorbers include cinnamate binding to polymer silicone, and specific examples thereof include polysilicone-15 and the like.

These oil-soluble ultraviolet absorbers nay be used in combination of two or more. In terms of acquiring a higher protective effect against UV-B and further against UV-A, it is more preferable to use three or more oil-soluble ultraviolet absorbers in combination.

The oil-soluble ultraviolet absorbers used in the present invention refer to ultraviolet absorbers that can dissolve in $C_{12-15}$ alkyl benzoate at 80° C. in an amount of at least 1 wt. % or more.

The content of the oil-soluble ultraviolet absorbers is not limited as long as the effects of the present invention are obtained. For example, the total content of the oil-soluble ultraviolet absorbers in the sunscreen composition is 10 wt. % or more, and preferably 10 to 25 wt. %.

The composite silicone particles used in the present invention have an average particle diameter of 10 μm or less, and a particle size distribution in the range of about 1 to 15 μm. Preferred examples of the composite silicone particles include those having a silicone resin. More preferred examples of the composite silicone particles include composite particles obtained by coating silicone rubber with a silicone resin, such as rubber-resin composite silicone particles; and still more preferred are rubber-resin composite silicone particles obtained by coating spherical silicone rubber with a silicone resin. Moreover, preferred examples of rubber-resin composite silicone particles include composite particles combined with vinyl dimethicone, vinyl diphenyl dimethicone, silsesquioxane, methicone silsesquioxane, etc. Preferred rubber-resin composite silicone particles are rubber-resin composite silicone particles having an average particle diameter of 10 μm or less, more preferably 2 to 10 μm, and even more preferably 2 to 8 μm. Specific examples of rubber-resin composite silicone particles include KSP-100 (average particle diameter: 5 μm), KSP-105 (average particle diameter: 2 μm), KSP-300 (average particle diameter: 5 μm), KMP-600 (average particle diameter: 5 μm), and KMP-605 (average particle diameter: 2 μm) (all produced by Shin-Etsu Chemical). These may be used singly or in combination of two or more.

The content of the composite silicone particles having an average particle diameter of 10 μm or less is not limited as long as the effects of the present invention are obtained, and the content may be suitably determined depending on the type of particles. For example, the content of the composite silicone particles in the sunscreen composition is 4 to 20 wt. %.

In the present invention, the use of the silicone particles above contributes to SPF and/or PA, as well as the feeling of slippery skin and the viscosity of the sunscreen composition.

In addition to the above-mentioned components, the sunscreen composition of the present invention may contain, if necessary, any other cosmetically or pharmacologically acceptable components. Examples of other components include solvents, surfactants, water-soluble ultraviolet absorbers, water, electrolytes, coating-forming agents, moisturizers, emollient agents, lubricants, preservatives, anti-inflammatory agents, refrigerants, chelating agents, neutralizing agents, antioxidants, flavoring agents, pigments, dyes, lubricants, emulsion stabilizers, defoaming agents, protective agents, pH adjusters, skin conditioning agents, thickeners, whitening agents, cell activators, sugars, amino acids, vitamins, and the like.

Examples of some of these other components are further shown below, although they do not limit the present invention. Specifically, salts, derivatives, adducts, complexes, or polymers of the components shown below can be used, as long as they do not impair the properties.

The solvent used in the sunscreen composition of the present invention is not limited as long as it can dissolve oil-soluble ultraviolet absorbers. Examples of the solvent used to dissolve oil-soluble ultraviolet absorbers include cyclopentasiloxane, dimethicone, $C_{12-15}$ alkyl benzoate, hydrogenated polyisobutene, isostearyl neopentanoate, erythrityl triethylhexanoate, pentaerythrityl tetraethylhexanoate, cetyl ethylhexanoate, ethylhexyl ethylhexanoate, methylpentanediol dineopentanoate, diethylpentanediol dineopentanoate, isononyl isononanoate, tri(caprylic/capric acid) glyceryl, cyclohexasiloxane, cyclotetrasiloxane, octamethyltrisiloxane, cyclomethicone, caprylyl methicone, diethylhexyl succinate, diisopropyl sebacate, and the like; preferably cyclopentasiloxane, dimethicone, $C_{12-15}$ alkyl benzoate, caprylyl methicone, erythrityl triethylhexanoate, and pentaerythrityl tetraethylhexanoate. These may be used singly or in combination of two or more.

The content of the solvent is not limited as long as the effects of the present invention are obtained. For example, the content of the solvent in the sunscreen composition is 10 to 50 wt. %, preferably 20 to 50 wt. %, and more preferably 20 to 45 wt. %.

Moreover, examples of surfactants include, but are not limited to, nonionic surfactants, silicone surfactants, cationic surfactants, anionic surfactants, and ampholytic surfactants.

Specific examples of nonionic surfactants include PEG hydrogenated castor oil, PEG isostearate, oleic acid polyglyceryl, PEG diisostearate, PEG triisostearate, glyceryl hydroxystearate, PEG dipolyhydroxystearate, and the like.

Examples of silicone surfactants include lauryl PEG polydimethylsiloxyethyl dimethicone, PEG polydimethylsiloxyethyl dimethicone, PEG methyl ether dimethicone, PEG/PPG butyl ether dimethicone, PEG dimethicone, PEG methyl ether dimethicone, and the like.

Examples of cationic surfactants include alkyl trimethyl ammonium chloride, such as stearyl trimethyl ammonium chloride; dialkyl dimethyl ammonium chloride, such as distearyl dimethyl ammonium chloride; benzalkonium chloride; and the like.

Examples of anionic surfactants include fatty acid salts, such as potassium stearate and triethanolamine stearate; alkyl sulfates, such as cetyl sodium sulfate; POE alkyl ether sulfates, such as POE alkyl (12,13) ether sulfate triethanolamine; N-acylmethyltaurine salts, such as sodium myristoyl methyltaurine; alkyl phosphates, such as diethanolamine cetyl phosphate; POE alkyl phosphates, such as POE cetyl ether sodium phosphate; N-acylamino acid salts, such as sodium N-stearoyl-L-glutamate, potassium N-stearoyl-L-glutamate, triethanolamine N-stearoyl-L-glutamate; and the like.

Examples of ampholytic surfactants include alkyl carboxymethyl hydroxyethyl imidazolinium betaine, such as 2-alkyl-N-carboxymethyl-N-hydroxyethyl imidazolinium betaine; alkyl amidopropyl betaine, such as lauramidopropyl betaine; alkyl hydroxysulfobetaine, such as lauryl hydroxysulfobetaine; and the like.

Preferred among these are nonionic surfactants and silicone surfactants. Specific examples thereof include PEG dipolyhydroxystearate, lauryl PEG polydimethylsiloxyethyl dimethicone, and the like. These may be used singly or in combination of two or more.

The content of the surfactant is also not limited, as long as the effects of the present invention are obtained. For example, the content of the surfactant in the sunscreen composition is 0.5 to 4 wt. %.

Further, in some cases, the sunscreen composition of the present invention may contain a water-soluble ultraviolet absorber as long as the effects of the present invention are obtained. Examples of water-soluble ultraviolet absorbers include phenylbenzimidazole sulfonic acid, terephthalylidine dicamphor sulfonic acid, oxybenzone-4, salts thereof, and the like; preferred are phenylbenzimidazole sulfonic acid, terephthalylidene dicamphor sulfonic acid, and salts thereof. These may be used singly or in combination of two or more; however, when three or more oil-soluble ultraviolet absorbers are mixed, it is more preferable that the sunscreen composition of the present invention contains only one or no water-soluble absorbent, so as to reduce the burden on the skin. Moreover, when the sunscreen composition of the present invention is in the form of a water-in-oil type emulsion in which the aqueous phase contains an electrolyte, it is desirable to use at most one water-soluble ultraviolet absorber so as not to affect the stability. The water-soluble ultraviolet absorber that can be used in this case is, for example, phenylbenzimidazole sulfonic acid or a salt thereof.

The content of the water-soluble ultraviolet absorber is also not limited, as long as the effects of the present invention are obtained. For example, the content of the water-soluble ultraviolet absorber in the sunscreen composition is 0 to 10 wt. %, and preferably 0 to 5 wt. %.

Further, when the sunscreen composition of the present invention contains water, the water is not limited. For example, purified water, distilled water, ion exchange water, or natural water can be used.

The content of water is also not limited, as long as the effects of the present invention are obtained. For example, the content of water in the sunscreen composition is 10 to 40 wt. %, preferably 15 to 30 wt. %, and more preferably 20 to 30 wt. %. When the sunscreen composition of the present invention contains an electrolyte, the presence of water is required. A water content of 10 wt. % or less makes it difficult for the sunscreen composition to stably contain an electrolyte, whereas an overly high water content may impair the water resistance of the sunscreen composition.

For the purpose of forming the sunscreen composition of the present invention into a stable water-in-oil type emulsion, it is desirable that the sunscreen composition contains an electrolyte. The electrolyte to be used is not particularly limited. For example, electrolytes usable in external preparations, particularly cosmetics and external-use drugs or quasi drugs, can be widely used.

A preferred example of the electrolyte used in the present invention is at least one member selected from the group consisting of inorganic salts, purine-based compounds, and water-soluble vitamins, water-soluble vitamin derivatives, and salts thereof.

Examples of mineral salts used in the present invention include chloride, sulfide, etc., of metal, such as sodium, potassium, magnesium, or calcium.

The purine-based compound in the present invention is a generic name for various derivatives having a purine nucleus as the skeleton, and salts thereof. The purine-based compound used in the present invention is not particularly limited as long as it is pharmacologically or cosmetically acceptable. Specific examples thereof include adenine, guanine, and deaminated products thereof; adenosine, guanosine, inosine, phosphates of adenosine (adenosine monophosphate (adenosine 5'-monophosphate), adenosine diphosphate, adenosine triphosphate, adenosine-3',5'-cyclic phosphate, etc.), phosphates of guanosine (guanosine monophosphate, guanosine diphosphate, guanosine triphosphate, etc.), phosphates of inosine (inosine monophosphate, inosine diphosphate, inosine triphosphate, etc.), and the like.

Examples of water-soluble vitamins and derivatives thereof used in the present invention include ascorbic acid, vitamin B group, lipoic acid, and derivatives thereof. Specific examples of derivatives of ascorbic acid include magnesium ascorbyl phosphate, sodium ascorbyl phosphate, disodium ascorbyl sulfate, glucoside ascorbate, glucosamine ascorbate, dehydroascorbic acid, and the like.

Salts of the various derivatives having a purine nucleus as the skeleton and salts of the water-soluble vitamins and the derivatives thereof above are not particularly limited as long as they are pharmacologically or cosmetically acceptable. Examples thereof include alkali metal salts, such as sodium salt and potassium salt; and alkaline earth metal salts, basic amino acid salts, ammonium salts, alkanolamine salts, and the like. Preferred among these salts are alkali metal salts; and more preferred are sodium salts.

Even more preferred among these are inorganic chloride, inorganic sulfide, and adenosine phosphate, ascorbic acid, ascorbic acid derivatives, and salts thereof; still more preferred are chloride and/or sulfide of sodium, magnesium, or calcium, and adenosine monophosphate, ascorbic acid, ascorbic acid derivatives, and salts thereof; and particularly preferred are sodium chloride, magnesium chloride, calcium chloride, adenosine monophosphate and salts thereof, and ascorbyl phosphate and salts thereof. In the present invention, the electrolytes may be used singly or in combination of two or more.

The content of the electrolyte is not limited as long as the effects of the present invention are obtained. For example, the content of the electrolyte in the sunscreen composition is 0.1 to 10 wt. %. In particular, when the sunscreen composition is in the form of a water-in-oil type emulsion, the content of the electrolyte in the sunscreen composition is preferably 0.5 to 5 wt. %, and more preferably 0.5 to 3 wt. %, in terms of stably maintaining the water-in-oil type emulsion form in an excellent state for a long period of time. Moreover, the content of the electrolyte per 100 parts by weight of water in the sunscreen composition in the form of a water-in-oil type emulsion is, for example, 1.5 to 40 parts by weight, preferably 2 to 20 parts by weight, more preferably 2 to 10 parts by weight, and particularly preferably 2 to 6 parts by weight.

The sunscreen composition of the present invention can suitably have a desired form, such as a water-in-oil type (W/O (water in oil)) emulsion or an oil-in-water type (O/W (oil in water)) emulsion. When the sunscreen composition of the present invention is in the form of an emulsion, it is further desirable to suitably maintain the emulsion form, in terms of obtaining the above-mentioned desired effects of the present invention. The suitable emulsion form indicates that oil drops of an oil-in-water type emulsion are stably present in the emulsion, or that water drops of a water-in-oil type emulsion are stably present in the emulsion. More specifically, for example, the following describes a case of the sunscreen composition of the present invention in the form of a water-in-oil type emulsion, which is mainly separated into two layers when allowed to stand. The upper layer is an oil phase, and the lower layer is a phase in which water drops so fine that they can hardly be visually observed are dispersed in oil. When water drops so fine that they can hardly be visually observed are substantially homogeneously dispersed in the oil in the lower layer, it can be said that the suitable water-in-oil type emulsion form is maintained. This reversible separation state is called creaming. On the other hand, when the water drops in the oil in the lower layer become so overly large that they can be visually observed, and the water drops are further combined to form an aqueous phase, which is then separated, it can be considered that the suitable emulsion form cannot be sufficiently maintained. In that case, the desired ultraviolet protection effects of the present invention may not be sufficiently acquired. From this viewpoint, in the sunscreen composition of the present invention in the form of an emulsion, particularly a water-in-oil type emulsion, maintaining the suitable emulsion form for a longer period of time is one of the important characteristics.

As described above, the sunscreen composition of the present invention comprising two or more oil-soluble ultraviolet absorbers and composite silicone particles having an average particle diameter of 10 μm or less can exhibit improved SPF. Moreover, in the present invention, the SPF of the sunscreen composition can be suitably set to a desired value depending on the purpose, by combining the components, such as the oil-soluble ultraviolet absorbers, with the above-mentioned composite silicone particles, and mixing them in the above-mentioned content range. Since the SPF value of the sunscreen composition of the present invention can thus be suitably determined, this composition can be used not only as a sunscreen composition with a relatively low SPF, which is intended for use in daily life, such as when staying indoors and when going out for a short period of time, but also as a sunscreen composition with a high SPF value, which is suitable for use in places exposed to high doses of ultraviolet radiation. The present invention is particularly suitable for a sunscreen composition with a high SPF value. When the target product is a sunscreen cosmetic or quasi drug for use in places exposed to high doses of ultraviolet radiation, the desired SPF value is 40 or more, and preferably 50 or more. For example, it is desirable to have an SPF value that allows the display of SPF50+, which is an indicator of ultraviolet UV-B protection ability in Japan.

Furthermore, the sunscreen composition of the present invention has an ultraviolet protection effect not only against UV-B, but also against UV-A. In particular, by containing three or more oil-soluble ultraviolet absorbers, the sunscreen composition of the present invention has a high protective effect against ultraviolet radiation in both the UV-B region and the UV-A region. Thus, both the PFA and SPF of the sunscreen composition of the present invention can be suitably set to desired values depending on the purpose of use, by combining the components, such as the above oil-soluble ultraviolet absorbers, with the above composite silicone particles, and suitably mixing them in the above content range. Although PA is displayed in various ways in different countries, as PFA values used as evaluation criteria for PA, a PFA value of 4 or more tends to be preferred for sunscreen compositions intended for use in places exposed to high doses of ultraviolet radiation. Accordingly, from the viewpoint of a composition having a high sunscreen effect, it is desirable that the composition has a high PA effect, as with SPF. For example, it is desirable to have a PFA value that allows the display of PA+++, which is an indicator indicating ultraviolet UV-A protection ability in Japan. That is, the sunscreen composition of the present invention can have a high SPF value and a high PFA value, preferably an SPF of 40 or more and a PFA of 5 or more, and more preferably an SPF of 50 or more (SPF50+) and a PFA of 8 or more (PA+++ or more in Japan).

Thus, according to the present invention, the SPF and PA of the sunscreen composition can be set to desired values. When applied to the skin, this sunscreen composition exhibits an excellent sunscreen effect.

Moreover, according to the present invention, the viscosity of the sunscreen composition is also not limited, and can be suitably determined depending on the desired form; however, a low viscosity is preferable in terms of achieving more excellent feeling of use, such as feeling of slippery skin. Such a viscosity is in the range of 100 to 1,000 mPa·s, and preferably 100 to 500 mPa·s, as measured by a Brookfield viscometer at 20° C.

Furthermore, it is desirable that the sunscreen composition of the present invention does not contain an ultraviolet scattering agent, such as metal oxide (e.g., zinc oxide or titanium oxide), in order to avoid whitening of the skin during use, and squeaky feeling when applied to the skin. Generally, ultraviolet scattering agents are used widely in many conventionally reported sunscreen agents with a high SPF. In the present invention, no incorporation of an ultraviolet scattering agent is useful to prevent uncomfortable feeling, such as whitening of the skin when the sunscreen composition is used. Note that even if an ultraviolet scattering agent is incorporated, the content of the ultraviolet scattering agent in the sunscreen composition is preferably 0.5 wt. % or less.

Examples of one embodiment of the sunscreen composition of the present invention include sunscreen compositions comprising at least two oil-soluble ultraviolet absorbers, rubber-resin composite silicone particles having an average particle diameter of 10 μm or less, a solvent, a surfactant, and water, wherein the oil-soluble ultraviolet absorbers are selected from the group consisting of ethylhexyl methoxycinnamate, octocrylene, diethylamino hydroxybenzoyl hexyl benzoate, polysilicone-15, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramethylbutylphenol, oxybenzone-3, and drometrizole trisiloxane. When an even higher protection effect against UV-A is imparted, it is preferable to use three or more oil-soluble ultraviolet absorbers, one of which is preferably selected from the group consisting of diethylamino hydroxybenzoyl hexyl benzoate, t-butyl methoxybenzoyl methane, bis-ethylhexyloxyphenol methoxyphenyl triazine, methylene-bis-benzotriazolyl tetramethylbutylphenol, oxybenzone-3, and drometrizole trisiloxane; and particularly preferably diethylamino hydroxybenzoyl hexyl benzoate.

Further, examples of another embodiment of the sunscreen composition of the present invention include sunscreen compositions obtained by further adding an aforementioned electrolyte to the above embodiment.

The sunscreen composition of the present invention may further contain optional components, such as, in particular, antioxidants, preservatives, emollient agents, pH adjusters, chelating agents, anti-inflammatory agents, etc., mentioned above.

Examples of antioxidants or preservatives suitable for the formulation in the present invention include tocopherol, dibutyl hydroxy toluene, pentylene glycol, catechins, benzoic acid, isopropyl methyl phenol, salicylic acid, parahydroxybenzoate, phenoxyethanol, and the like.

Examples of emollient agents suitable for the formulation in the present invention include dihydrocholesterol, hexyldecyl isostearate, jojoba oil, squalane, cholesteryl stearate, pentaerythrityl tetraethylhexanoate, polyglyceryl decaisostearate, hexyldecyl ethylhexanoate, PEG lanolin, isodecyl neopentanoate, chimyl alcohol, baty alcohol, stearoyl inulin, hydrogenated polyisobutene, tri(caprylic/capric acid) glyceryl, and the like.

Examples of pH adjusters and chelating agents suitable for the formulation in the present invention include aminomethyl propanol, aminomethyl propanediol, triethanolamine, citric acid and other organic acids, EDTA, and the like.

Examples of anti-inflammatory agents suitable for the formulation in the present invention include glycyrrhizic acid or salts thereof, glycyrrhetic acid or fatty acid esters thereof, tranexamic acid, bromelain, camomile extract, and the like. In the present invention, it is preferable to use an anti-inflammatory agent in combination with an aforementioned electrolyte, such as a purine-based compound (e.g., adenosine phosphate), a water-soluble vitamin, or a water-soluble vitamin derivative or a salt thereof. The combined use is expected to result in the effect of improving skin disorders and the effect of improving skin functions.

The sunscreen composition of the present invention may further contain peppermint (menthol) and a flavoring agent (essential oil, synthetic perfume, etc.), as necessary. For example, peppermint is effective to impart coolness and aroma to the sunscreen composition. From this viewpoint, it is preferable to mix peppermint into the sunscreen composition. Further, an essential oil can improve the feeling of slippery skin due to its oiliness, and can be used as a flavoring agent that is gentle to skin. It is thus preferable to mix an essential oil into the sunscreen composition. The essential oil to be mixed is not particularly limited as long as it is oil, and conventionally known essential oils can be used. Particularly when used in combination with a purine-based compound, such as adenosine phosphate, the essential oil is preferably selected from star anise oil, cedar leaf oil, Atlas cedar oil, *Lavandula hybrida* oil, lime oil, peppermint oil, *Pinus sylvestris* oil, rosemary oil, and turpentine oil; and more preferably selected from star anise oil, *Pinus sylvestris* oil, and *Lavandula hybrida* oil.

From these viewpoints, examples of another embodiment of the sunscreen composition of the present invention includes sunscreen compositions comprising at least two oil-soluble ultraviolet absorbers, rubber-resin composite silicone particles having an average particle diameter of 10 μm or less, a solvent, a surfactant, an electrolyte, an anti-inflammatory agent, an essential oil, and water, wherein the oil-soluble ultraviolet absorbers are selected from the group consisting of ethylhexyl methoxycinnamate, octocrylene, diethylamino hydroxybenzoyl hexyl benzoate, polysilicone-15, homosalate, t-butyl methoxybenzoyl methane, ethylhexyl salicylate, ethylhexyl triazone, bis-ethylhexyloxyphenol methoxyphenyl triazine, methylene-bis-benzotriazolyl tetramethylbutylphenol, oxybenzone-3, and drometrizole trisiloxane.

The form of the sunscreen composition of the present invention may be a single layer or multilayer, without limitation, and various conventionally known forms can be employed depending on the purpose. Moreover, the sunscreen composition of the present invention can be further used as a liquid with a sunscreen effect, such as lotion, milky lotion, and essence; a make-up cosmetic, such as makeup base, foundation, and lipstick; and particularly a liquid make-up cosmetic.

Although the sunscreen composition of the present invention can suitably have a desired form, such as a water-in-oil type emulsion or an oil-in-water type emulsion, a water-in-oil type emulsion form is preferred in terms of enhancing water resistance.

The sunscreen composition of the present invention can be produced by suitably mixing the components, such as the above oil-soluble ultraviolet absorbers, and the composite silicone particles having an average particle diameter of 10 μm or less by a conventionally known method so that the desired SPF value, the desired PFA value, the desired viscosity, and/or the desired form are obtained, depending on the purpose.

The number of times of applying the sunscreen composition of the present invention to the skin is not particularly limited. For example, the effect can be sufficiently obtained by applying the sunscreen composition in an amount of about 2 mg per cm$^2$ once in every two hours.

The sunscreen composition of the present invention exhibits an excellent sunscreen effect when applied to the skin. In particular, the sunscreen composition of the present invention can exhibit a high effect against both SPF and PA. The sunscreen effect can be sufficiently exerted in a place exposed to high doses of ultraviolet radiation. Moreover, the SPF and PA of the sunscreen composition of the present invention can be suitably set to desired values. This sunscreen composition can exhibit an excellent sunscreen effect against both SPF and PA when applied to the skin.

When the sunscreen composition of the present invention is formed into a water-in-oil type emulsion, the sunscreen composition of the present invention particularly has water resistance against sweat, water, etc. Accordingly, when the sunscreen composition of the present invention is formed into a water-in-oil type emulsion, the sunscreen composition of the present invention has a desired SPF and a desired PA, while having further excellent effects that the sunscreen composition is more hardly removed from the skin due to sweat, water, etc., and inhibits or prevents reduction in the ultraviolet protection effect over time. Moreover, when the sunscreen composition of the present invention is formed into a liquid water-in-oil type emulsion, the sunscreen composition of the present invention has a further excellent effect in terms of better feeling of slippery skin. Furthermore, when the sunscreen composition of the present invention, particularly in the form of a water-in-oil type emulsion, contains a specific amount of electrolyte, this composition particularly has excellent stability over time.

Accordingly, the sunscreen composition of the present invention is not only useful for use in daily life, such as when staying indoors and when going out for a short period of time, but also exhibits excellent ultraviolet protection ability and water resistance in places exposed to high doses of ultraviolet radiation, such as places where outdoor activities and outdoor sports are enjoyed, for which an even higher ultraviolet protection effect is required. This sunscreen composition can also be effectively used as a sunscreen composition that is resistant to water and sweat, and that is comfortable for use.

In addition, according to one embodiment of the present invention, a sunscreen composition that is less likely to cause whitening of the skin when applied to the skin can be produced. Many of conventional sunscreen compositions cause unnatural whitening of the skin when applied to the skin, thereby spoiling the feeling of use. Since the sunscreen composition of the present invention is less likely to cause whitening of the skin when applied to the skin, the feeling of use in this regard can also be improved. Moreover, according to one embodiment of the present invention, a sunscreen composition in the form of a water-in-oil type emulsion, which even contains an electrolyte, such as adenosine phosphate, exhibits a high sunscreen effect, as described above, while enhancing a function derived from the electrolyte, such as normalization of the moisture permeability function of the skin, thereby making the sunscreen composition gentler to the skin. Furthermore, since the sunscreen composition of the present invention can be easily washed off from the skin after use, the composition has advantages in that it is not necessary to apply excessive stimulation (e.g., excessively rub the skin) to wash off the sunscreen composition, and in that inconvenience regarding difficulty in washing off, and discomfort are reduced.

Accordingly, the present invention can be said to provide use of two or more oil-soluble ultraviolet absorbers and composite silicone particles having an average particle diameter of 10 μm or less for improving the ultraviolet protection effect of the sunscreen composition, in terms of the SPF value, water resistance, PAF value, and/or stability over time. Moreover, owing to the use of two or more oil-soluble ultraviolet absorbers and composite silicone particles having an average particle diameter of 10 μm or less, the present invention can be said to provide a method for improving the ultraviolet protection effect of the sunscreen composition comprising the oil-soluble ultraviolet absorbers, in terms of the SPF value, water resistance, PAF value, and/or stability over time. When the use and method are provided, the sunscreen composition and the structural components thereof, such as oil-soluble ultraviolet absorbers and composite silicone particles having an average particle diameter of 10 μm or less, the content of each component, the production method, the method for applying the sunscreen composition, and the like, are explained in the same manner as above.

EXAMPLES

The present invention is described below with reference to Examples; however, the present invention is not limited to these Examples.

Test Example 1

1. Production of Sunscreen Composition

The components shown in Table 1 below were mixed at each mixing ratio, thereby preparing emulsion-like, water-in-oil type sunscreen compositions (Examples 1 to 3). Note that the unit of each mixing ratio in the table is wt. %.

TABLE 1

|  | Ex. 1 | Ex. 2 | Ex. 3 | Comp. Ex. 1 |
|---|---|---|---|---|
| Ethylhexyl methoxycinnamate *1 | 7 | 7 | 7 | 7 |
| Octocrylene *2 | 3 | 3 | 3 | 3 |
| Diethylamino hydroxybenzoyl hexyl benzoate *3 | 4 | 4 | 4 | 4 |
| Polysilicone-15 *4 | 3.5 | 3.5 | 3.5 | 3.5 |
| (Vinyl dimethicone/methicone silsesquioxane) crosspolymer (average particle diameter: 5 μm) *5 | 4 | 4 | 4 | 0 |
| (Vinyl dimethicone/methicone silsesquioxane) crosspolymer (average particle diameter: 12 μm) *6 | 0 | 0 | 0 | 4 |

TABLE 1-continued

|  | Ex. 1 | Ex. 2 | Ex. 3 | Comp. Ex. 1 |
|---|---|---|---|---|
| Dimethicone *7 | 0 | 0.2 | 0 | 0 |
| Dimethicone *8 | 1 | 0.8 | 1 | 3 |
| Caprylyl methicone *9 | 2.5 | 2.5 | 2.5 | 0 |
| Diphenylsiloxy phenyl trimethicone *10 | 0.3 | 0.3 | 0.3 | 0.5 |
| $C_{12-15}$ Alkyl benzoate *11 | 5 | 5 | 5 | 3 |
| Cyclopentasiloxane *12 | 14 | 14 | 14 | 16 |
| Cyclopentasiloxane/dimethiconol *13 | 0 | 0 | 0.5 | 0 |
| Cyclopentasiloxane/trimethylsiloxysilicate *14 | 0.5 | 0.5 | 0.5 | 0.5 |
| Cyclopentasiloxane/polymethylsilsesquioxane *15 | 0 | 0 | 0 | 1 |
| Polymethylsilsesquioxane (average particle diameter: 6 μm) *16 | 3 | 3 | 3 | 4 |
| Polymethylsilsesquioxane *17 | 2 | 2 | 2 | 0 |
| Phenylbenzimidazole sulfonic acid *18 | 1.5 | 1.5 | 1.5 | 1.5 |
| Lauryl PEG-9 polydimethylsiloxyethyl dimethicone *19 | 2.4 | 2.4 | 2.4 | 2.5 |
| PEG-30 dipolyhydroxystearate *20 | 0.2 | 0.2 | 0.2 | 0.2 |
| Ethanol | 7.5 | 7.5 | 7.5 | 7.5 |
| Adenosine 5'-monophosphate | 0.5 | 0.5 | 0.5 | 0.5 |
| Antioxidant, preservative | Suitable amount | Suitable amount | Suitable amount | Suitable amount |
| Chelating agent, pH adjuster, emollient agent, flavoring agent | Suitable amount | Suitable amount | Suitable amount | Suitable amount |
| Moisturizer, anti-inflammatory agent | Suitable amount | Suitable amount | Suitable amount | Suitable amount |
| Water | 25-30 | 25-30 | 25-30 | 25-30 |
| Total | 100 | 100 | 100 | 100 |

*1: trade name "Uvinul MC80N" (produced by BASF)
*2: trade name "Eusolex OCR" (produced by Merck)
*3: "Uvinul A Plus Granular" (produced by BASF)
*4: trade name "Parsol SLX" (produced by DSM)
*5: trade name "KSP-100" (produced by Shin-Etsu Chemical)
*6: trade name "KSP-101" (produced by Shin-Etsu Chemical)
*7: trade name "KF-96A-6CS" (produced by Shin-Etsu Chemical)
*8: trade name "KF-96A-50000CS" (produced by Shin-Etsu Chemical)
*9: trade name "SS-3408" (produced by Dow Corning Toray)
*10: trade name "KF-56A" (produced by Shin-Etsu Chemical)
*11: trade name "Crodamol AB" (produced by Croda)
*12: trade name "SH245 Fluid" (produced by Dow Corning Toray)
*13: trade name "1501 Fluid" (produced by Dow Corning Toray)
*14: trade name "KF-7312J" (produced by Shin-Etsu Chemical)
*15: trade name "SilForm Flexible Fluid" (produced by Momentive)
*16: trade name "Tospearl 2000B" (produced by Momentive)
*17: trade name "KMP-590" (produced by Shin-Etsu Chemical)
*18: trade name "Parsol HS" (produced by DSM)
*19: trade name "KF-6038" (produced by Shin-Etsu Chemical)
*20: trade name "Cithrol DPHS AP" (produced by Croda)

As a Comparative Example, a sunscreen composition was produced in the same manner using a (vinyl dimethicone/methicone silsesquioxane) crosspolymer having an average particle diameter of 12 μm (Comparative Example 1), in place of the (vinyl dimethicone/methicone silsesquioxane) crosspolymer having an average particle diameter of 5 μm shown in Table 1.

2. Measurement of SPF

The SPF values of the sunscreen compositions produced in Examples 1 to 3 and Comparative Example 1 were measured in an in vitro system.

Specifically, the sunscreen compositions of Examples 1 to 3 and Comparative Example 1 were each put on the entire surface of different plates (Helioplate (registered trademark) HD6, produced by HerioScreen Lab.) in the form of a small spot using a pipette. The amount of each sunscreen composition was 28.7±0.3 mg per plate. Then, the sunscreen composition was quickly spread over the entire plate with light force, and then uniformly applied to the entire plate. After the plate was allowed to stand at room temperature in a dark place for 15 minutes, the SPF values of the plate were measured using UV-2000S (produced by Labsphere), and their average value was obtained.

TABLE 2

|  | Ex. 1 | Ex. 2 | Ex. 3 | Comp. Ex. 1 |
|---|---|---|---|---|
| SPF value | 85 | 94 | 77 | 39 |

3. Results

As is clear from Table 2, the sunscreen compositions of Examples 1 to 3 showed SPF that was significantly superior to the sunscreen composition of Comparative Example 1. This demonstrated that the sunscreen compositions of Examples 1 to 3 can further enhance the effect of ultraviolet absorbers. Although there may be a gap between the SPF values measured in the in vitro system and SPF values evaluated on humans, depending on the measurement situation, etc., it is recognized from the above values obtained in Examples 1 to 3 that an SPF value of at least 40 or more will be obtained in humans. In addition, because oil-soluble ultraviolet absorbers having a protective effect against UV-A were used in combination in Examples 1 to 3, it is also recognized that high PA will be obtained, as with SPF.

Moreover, the sunscreen compositions of Examples 1 to 3, which were in the form of water-in-oil type emulsions, have water resistance against sweat, water, etc. This revealed the following: the sunscreen compositions of Examples 1 to 3 further have the effect that they are hardly removed from the skin; they are not only useful for use in daily life, such as when staying indoors and when going out for a short period of time, but also useful in places exposed to high doses of ultraviolet radiation, for which an even higher ultraviolet protection effect is required, in terms of their excellent ultraviolet protection ability and water resistance; and they can be effectively used as sunscreen compositions resistant to water and sweat.

Furthermore, although the results are not shown, the sunscreen compositions of Examples 1 to 3, which did not contain metal powder, such as titanium oxide, did not cause unnatural whitening of the skin when applied to the skin, which was typical in sunscreen compositions with a high SPF. Thus, these sunscreen compositions were satisfactory. In addition, the viscosity of the sunscreen compositions was in the desired low viscosity range. The feeling of slippery skin of the sunscreen compositions met expectations, unlike sunscreen preparations having a high viscosity.

Test Example 2

Examples 4 to 6

Production of Sunscreen Composition

The components shown in Table 3 below were mixed at each mixing ratio, thereby preparing water-in-oil type sunscreen compositions (Examples 4 to 6). Note that the unit of each mixing ratio in the table is wt. %. The viscosity of the compositions of Examples 1 to 3 was 150 to 250 mPa·s as measured by a Brookfield viscometer at 20° C.

TABLE 3

| Display name | Ex. 4 | Ex. 5 | Ex. 6 |
|---|---|---|---|
| Ethylhexyl methoxycinnamate *1 | 7 | 7 | 7 |
| Octocrylene *2 | 3 | 2.5 | 3.5 |
| Diethylamino hydroxybenzoyl hexyl benzoate *3 | 3 | 3 | 3 |
| Polysilicone-15 *4 | 3 | 3 | 3 |
| (Vinyl dimethicone/methicone silsesquioxane) crosspolymer *5 | 4 | 4 | 4 |
| Polymethylsilsesquioxane *6 | 3 | 3 | 3 |
| Phenylbenzimidazole sulfonic acid *7 | 0 | 1 | 0 |
| Dipotassium glycyrrhetinate | 0.05 | 0.05 | 0.05 |
| Stearyl glycyrrhetinate | 0.05 | 0.05 | 0.05 |
| Sodium hyaluronate | 0.001 | 0.001 | 0.001 |
| Sodium chloride, Adenosine 5'-monophosphate | 0.5-1 | 0.5-1 | 0.5-1 |
| Solvent, emollient agent | Suitable amount | Suitable amount | Suitable amount |
| Surfactant, antioxidant, preservative | Suitable amount | Suitable amount | Suitable amount |
| Chelating agent, pH adjuster, refrigerant, flavoring agent | Suitable amount | Suitable amount | Suitable amount |
| Water | 24-28 | 24-28 | 24-28 |
| Total | 100 | 100 | 100 |

*1: trade name "Uvinul MC80N" (produced by BASF)
*2: trade name "Eusolex OCR" (produced by Merck)
*3: "Uvinul A Plus Granular" (produced by BASF)
*4: trade name "Parsol SLX" (produced by DSM)
*5: trade name "KSP-100" (produced by Shin-Etsu Chemical)
*6: trade name "Tospearl 2000B" (produced by Momentive), trade name "KMP-590" (produced by Shin-Etsu Chemical)
*7: trade name "Parsol HS" (produced by DSM)

Test Example 2-1

Evaluation of SPF of Sunscreen Composition of Example 4

The SPF value of the sunscreen composition of Example 4 produced as described above was measured according to the International Standard ISO 24444. Specifically, the SPF value was measured in the following manner.

The sunscreen composition of Example 4 was applied to 10 subjects, and the testing portion was a site between the back shoulder blade and the waist. The application area of each subject was 5 cm×7 cm, and 70 mg of the sunscreen composition was spread with the fingertips over the entire site for about 30 seconds. Ultraviolet irradiation on the testing portion was started 15 minutes after application. The light source of ultraviolet irradiation used was a xenon arc solar simulator (Ushic Optical Maodulex, produced by Ushio Inc.) equipped with a filter system with 1-mm-thick Schott WG320 and UG11 filters, and the testing portion was irradiated with radiation light including UVB (wavelength: 290 to 320 nm). The number of radiation fields was 6, and the area of each field was 0.5 cm². The radiation level was amplified in an equal rate of 1.10. The SPF value of each subject was calculated as the ratio of MED of the applied portion/MED of the unapplied portion in each subject. MED (minimal erythema dose) was determined by visually observing the skin response 24±4 hours after irradiation. Note that MED indicates the minimum dose of ultraviolet radiation (time) in which slight erythema is observed in the skin. The SPF of the sunscreen composition was determined as the average of the SPF values obtained in this manner. Based on the thus-determined SPF value, the SPF display according to the specific classification of each country is determined. Table 2 shows the results.

TABLE 4

| | Average (n = 10) |
|---|---|
| SPF value | 55.3 |

As is clear from Table 4, the average value of the SPF values of the sunscreen composition of Example 4 was 55.3. The results of this test showed that the sunscreen composition of Example 4 had an SPF of 50 or more.

Moreover, since the sunscreen composition of Example 4 is in the form of a liquid water-in-oil type emulsion form, this composition also has water resistance against sweat, water, etc., and is hardly removed from the skin during use. This revealed that this sunscreen composition is not only useful for use in daily life, such as when staying indoors and when going out for a short period of time, but also useful in places exposed to high doses of ultraviolet radiation, for which an even higher ultraviolet protection effect is required, in terms of its excellent ultraviolet protection ability and water resistance; and that this sunscreen composition can also be effectively used as a sunscreen composition resistant to water and sweat. Furthermore, the sunscreen composition of Example 4, which contains adenosine phosphate, is expected to contribute to the maintenance and improvement of the moisture permeability function of the skin.

Test Example 2-2

Evaluation of SPF and PA of Sunscreen Composition of Example 5

The SPF value of the composition of Example 5 produced as described above was evaluated in the same manner as in Test Example 2-1, and the PFA value of the composition was evaluated according to the measurement standard guidelines of the Japan Cosmetic Industry Association.

The sunscreen composition of Example 5 was applied to 10 subjects, and the testing portion was a site between the back shoulder blade and the waist. The application area of each subject was 4 cm×6 cm, and 48 mg of the sunscreen composition was spread with the fingertips over the entire site for about 30 seconds. Ultraviolet irradiation on the testing portion was started 15 minutes after application. The light source of ultraviolet irradiation used was a xenon arc solar simulator (Ushio Optical Maodulex, produced by Ushio Inc.) equipped with a filter system with 1-mm-thick Schott WG320 and UG11 filters, and the testing portion was irradiated with radiation light including UVA (wavelength: 320 to 400 nm). The number of radiation fields was 6, and the area of each field was 0.5 cm². The radiation level was amplified in an equal rate of 1.10. The PFA value of each subject was calculated as the ratio of MPPD of the applied portion/MPPD of the unapplied portion in each subject. MPPD (minimal persistent pigment darkening dose; was determined 2 to 4 hours after the completion of irradiation. Note that MPPD indicates the minimum dose of ultraviolet radiation in which slight darkening of the skin is observed in almost the entire radiation field 2 to 4 hours after the completion of irradiation. The PFA value of the sunscreen composition was determined as the average of the PFA values obtained in this manner. Based on the thus-determined PFA value, the PA display according to the specific classification of each country is determined. Table 3 shows the results.

TABLE 5

| | Average (n = 10) |
|---|---|
| SPF value | 54.0 |
| PFA value | 8.3 |

As is clear from Table 5, the average value of the SPF values of the sunscreen composition of Example 5 was 54.0. The results of this test showed that the sunscreen composition of Example 5 also had an SPF of 50 or more. Further, the results showed that the PFA value of the sunscreen composition of Example 5 was also 8 or more. It was thus revealed that this sunscreen composition had a remarkably high protective effect against both UVA and UVB.

Moreover, since the sunscreen composition of Example 5 is also in the form of a liquid water-in-oil type emulsion, this composition has water resistance against sweat, water, etc., and is hardly removed from the skin during use, as with Example 4. This revealed that this sunscreen composition is not only useful for use in daily life, such as when staying indoors and when going out for a short period of time, but also remarkably useful in places exposed to high doses of ultraviolet radiation, for which an even higher ultraviolet protection effect is required, in terms of its excellent ultraviolet protection ability and water resistance, as described above; and that this sunscreen composition can be effectively used as a sunscreen composition resistant to water and sweat. Furthermore, the sunscreen composition of Example 5, which also contains adenosine phosphate, is expected to contribute to the maintenance and improvement of the moisture permeability function of the skin.

Test Example 2-3

Evaluation of SPF and PA of Sunscreen Composition of Example 6

The SPF value and PFA value of the composition of Example 6 produced as described above were evaluated in the same manner as in Test Example 2-2. Table 4 shows the results.

TABLE 6

| | Average (n = 10) |
|---|---|
| SPF value | 53.3 |
| PFA value | 8.1 |

As is clear from Table 6, the average value of the SPF values of the sunscreen composition of Example 6 was 53.3. The results of this test showed that the sunscreen composition of Example 6 also had an SPF of 50 or more. Further, the results showed that the PFA value of the sunscreen composition of Example 6 was also 8 or more. It was thus revealed that this sunscreen composition also had a remarkably high protective effect against both UVA and UVB.

Moreover, since the sunscreen composition of Example 6 is also in the form of a liquid water-in-oil type emulsion, this composition has water resistance against sweat, water, etc., and is hardly removed from the skin during use, as with Examples 4 and 5. This revealed that this sunscreen composition is not only useful for use in daily life, such as when staying indoors and when going out for a short period of time, but also remarkably useful in places exposed to high doses of ultraviolet radiation, for which an even higher ultraviolet protection effect is required, in terms of its excellent ultraviolet protection ability and water resistance, as described above; and that this sunscreen composition can also be effectively used as a sunscreen composition resistant to water and sweat. Furthermore, the sunscreen composition of Example 6, which also contains adenosine phosphate, is expected to contribute to the maintenance and improvement of the moisture permeability function of the skin.

Test Example 3

Evaluation of Whitening by Application of Sunscreen Composition of Example 6, and Confirmation of Washing Properties Next, whitening of the skin by application of the sunscreen composition of Example 6 was tested by comparison. The whitening evaluation was performed using the sunscreen composition of Example 6 and four commercially available sunscreen agents (Comparative Examples 2 to 5), described later, by comparing their degrees of whitening. Specifically, the evaluation of whitening by application was performed using urethane elastomer having touch and elasticity close to that of the human skin (Bio Skin, produced by Beaulax). For the purpose of confirming the degree of whitening by application, the sunscreen composition of Example 6 and the sunscreen agents of Comparative Examples 2 to 5 were each taken in an amount of about 30 mg, and applied and spread to the urethane elastomer so as to form a circle about 2.5 cm in diameter. The degree of whitening was visually confirmed. FIG. 1 shows the results.

Here, the four commercially available sunscreen agents (Comparative Examples 2 to 5) are described. All of these sunscreen agents contain only one oil-soluble ultraviolet absorber (ethylhexyl methoxycinnamate). More specifically, the sunscreen agent of Comparative Example 2 contains ethylhexyl methoxycinnamate, phenylbenzimidazole sulfonic acid, polymethylsilsesquioxane, zinc oxide, a flavoring agent, menthol, *Mentha piperita* leaf extract, etc. The sunscreen agent of Comparative Example 3 contains ethylhexyl methoxycinnamate, polymethylsilsesquioxane, zinc oxide, talc, silica, a flavoring agent, sodium acetyl hyaluronate, etc. The sunscreen agent of Comparative Example 4 contains ethylhexyl para-methoxycinnamate, zinc oxide, titanium oxide, silicic acid, sericite, hydroxyapatite, a flavoring agent, menthol, sage extract, seaweed extract, etc. The sunscreen agent of Comparative Example 5 contains octyl methoxycinnamate, polymethyl methacrylate, zinc oxide, titanium oxide, aluminium hydroxide, silica, menthol, peppermint oil, etc.

Further, the sunscreen composition of Example 6 and the four commercially available sunscreen agents (Comparative Examples 2 to 5) were used to evaluate the washing properties (ease of washing off from the skin). Specifically, the sunscreen composition of Example 6 and the sunscreen agents of Comparative Examples 2 to 5 were each taken in an amount of about 0.25 g, and applied to a cotton cloth cut into a 3 cm×3 cm square. The cotton cloth after application was immersed in a 10% dilute solution of a commercially available body soap (trade name: UL-OS Skin Wash, produced by Otsuka Pharmaceutical Co., Ltd.) in tap water (hardness: 40 ppm), and left in a hot bath at 50° C. for 1.5 hours, followed by water washing and drying. After drying, the amount of the sunscreen composition or sunscreen agent remaining in each cotton cloth was evaluated by weight.

Figure 2:
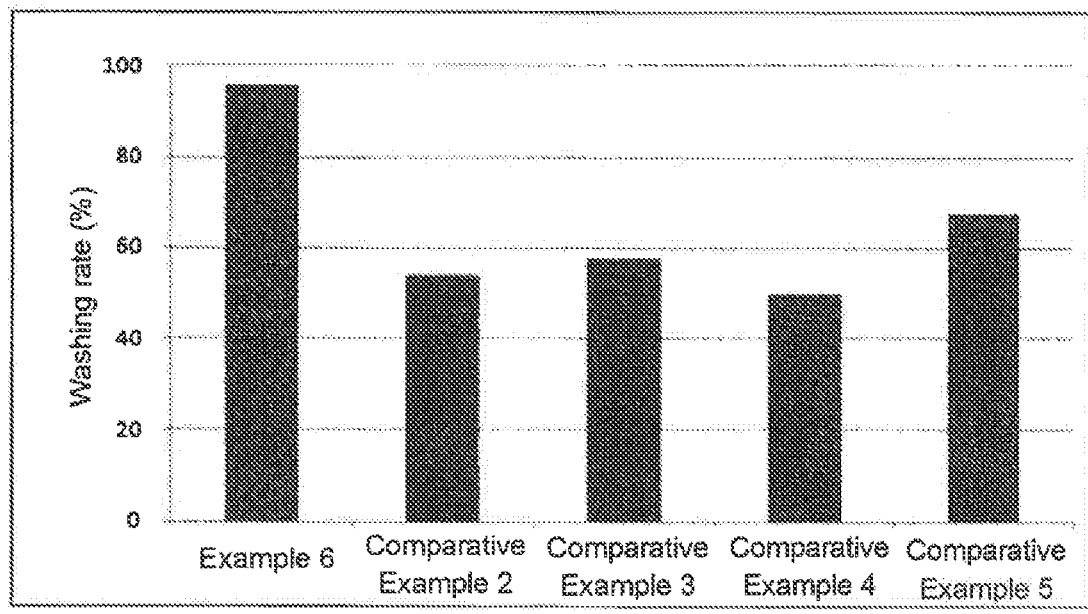
FIG. 2 is a graph showing the results of the evaluation of washing properties.

FIG. 2 shows the results. The washing properties were expressed as a washing rate (%) determined by the following equation: ((application amount to cotton cloth−remaining amount in cotton cloth)/application amount to cotton cloth)× 100 (n=3, average value). FIG. 2 revealed that the sunscreen composition of Example 6 had a much higher washing rate, and that it was very easily washed off from the skin, compared to the sunscreen agents of Comparative Examples 2 to 5.

As is clear from the above results, in spite of its high SPF and high PA, the sunscreen composition of Example 6 did not cause unnatural whitening of the skin when applied to the skin, which was typical in conventional sunscreen agents with a high SPF. Thus, this sunscreen composition was very satisfactory. In addition, the problem of difficulty in washing off, which was typical in conventional sunscreen agents with a high SPF, was not observed. This sunscreen composition was also very satisfactory in this respect. The same effects as those of the sunscreen composition of Example 6 are obtained in the sunscreen compositions of Examples 4 and 5 as well. Furthermore, the viscosity of the sunscreen compositions was in the desired low viscosity range, and the feeling of slippery skin met expectations, unlike sunscreen preparations having a high viscosity.

Test Example 4

1. Production of Sunscreen Composition

The components shown in Table 7 below were mixed at each of the mixing ratios shown in Table 8, thereby preparing sunscreen compositions in the form of water-in-oil type emulsions. Note that the unit of each mixing ratio in the table is wt. %. Specifically, components 1 to 9 in Table 7 were mixed, and uniformly dispersed and dissolved at 60° C., thereby preparing an oil phase A. Separately, components 10 to 15 in Table 7 were mixed and uniformly dissolved, and component 14 was used to adjust the pH to 7, thereby preparing an aqueous phase B. The oil phase A and the aqueous phase B were heated to 60° C., and the aqueous phase B was added to the oil phase A while stirring the oil phase A at 1,400 rpm using a mixer (T.K. ROBO MICS, produced by Tokushu Kika Kogyo). After stirring, component 16 was added, and the mixture was emulsified by stirring again at 1,400 rpm, thereby obtaining sunscreen compositions of Examples 7 to 17 shown in Table 8.

TABLE 7

| | Component name |
|---|---|
| 1 | Cyclopentasiloxane (trade name: "SH245 Fluid" (produced by Dow Corning Toray)) |
| 2 | Hydrogenated polyisobutene |
| 3 | Ethylhexyl methoxycinnamate (trade name: "Uvinul MC80N" (produced by BASF)) |
| 4 | Octocrylene (trade name: "Eusolex OCR" (produced by Merck)) |
| 5 | Diethylamino hydroxybenzoyl hexyl benzoate (trade name: "Uvinul A Plus Granular" (produced by BASF)) |
| 6 | Lauryl PEG-9 polydimethylsiloxyethyl dimethicone (trade name "KF-6038" (produced by Shin-Etsu Chemical)) |
| 7 | $C_{12-15}$ Alkyl benzoate (trade name "Crodamol AB" (produced by Croda)) |
| 8 | Polymethylsilsesquioxane (trade name "Tospearl 2000B" (produced by Momentive)) |
| 9 | (Vinyl dimethicone/methicone silsesquioxane) crosspolymer (average particle diameter: 5 μm) (trade name "KSP-100" (produced by Shin-Etsu Chemical)) |
| 10 | Glycerol (trade name: "Concentrated Glycerin" (produced by Kao Corporation)) |
| 11 | Sodium chloride |
| 12 | Adenosine 5'-monophosphate |
| 13 | Magnesium ascorbyl phosphate (produced by Wako Pure Chemical Industries) |

TABLE 7-continued

| | Component name |
|---|---|
| 14 | Aminomethyl propanediol (produced by GOO Chemical) |
| 15 | Water |
| 16 | Ethanol |

2. Stability Test

About 15 g of each sample was placed in a test tube, and the test tube was covered with a lid. After incubation in a 60° C. constant-temperature water bath for 4 to 7 days, the state of each sunscreen composition was observed. Specifically, the above sunscreen compositions were in the form of water-in-oil type emulsions, which were mainly separated into two layers when allowed to stand after production. The upper layer was an oil phase, and the lower layer was an emulsion phase in which water drops so fine that they could hardly be visually observed were dispersed in oil. The state was stable. Then, after incubation in the above 60° C. constant-temperature water bath for 4 to 7 days, the state of each sunscreen composition was visually observed.

3. Results

The sunscreen compositions of Examples 7 to 17 showed a stable state when allowed to stand after the production thereof as described above. Thus, the desired sunscreen compositions were obtained. Based on the results of Test Examples 1 to 3, it can be easily understood that the sunscreen compositions produced in Test Example 4 also exhibit the desired SPF values and PFA values, and that these compositions also have excellent water resistance because of their water-in-oil type emulsion form. It was thus revealed that according to the present invention, sunscreen compositions with an excellent ultraviolet protection effect can be obtained.

The sunscreen compositions obtained in this test example are in the form of excellent single-layer water-in-oil type emulsions, which are separated into two layers when allowed to stand. The reversible separation state of an emulsion that seems to have separate two layers at first glance, but easily returns to a homogeneous single-layer emulsion form by shaking is called creaming. In this test example, if a sunscreen composition returns to a homogeneous single-layer emulsion form by shaking, the stability of the sunscreen composition after storage is evaluated as good "+." On the other hand, examples of water-in-oil type emulsions with insufficient stability include those that undergo irreversible separation, whereby they do not return to a homogeneous emulsion form even by shaking. For example, a portion of the water drops combines to form water, which is excluded from the emulsion phase. In this test example, if irreversible separation is confirmed in a sunscreen composition after storage, the stability of the sunscreen composition is evaluated as insufficient "−."

As shown in Table 8, such irreversible separation was observed in Examples 7 to 10 after incubation for 4 days. The same tendency was also observed even after incubation for 7 days, and irreversible separation was confirmed in Examples 7 to 10 as well. In contrast, the sunscreen compositions of Examples 11 to 17 sufficiently maintained the suitable emulsion form even after incubation.

These results demonstrated that when 0.5 wt. % or more of electrolyte was mixed in the sunscreen composition of the present invention, the resulting sunscreen composition had the desired SPF value, PFA value, and water resistance, as well as remarkably excellent stability over time.

TABLE 8

| Component | Ex. 7 | Ex. 8 | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|---|---|
| 1 | 24 | Suitable amount | Suitable amount | Suitable amount | Suitable amount | Suitable amount | Suitable amount | Suitable amount | Suitable amount | Suitable amount | Suitable amount |
| 2 | 10 | 10 | 10 | 10 | 10 | 10 | 10 | 10 | 10 | 10 | 10 |
| 3 | 7.5 | 7.5 | 7.5 | 7.5 | 7.5 | 7.5 | 7.5 | 7.5 | 7.5 | 7.5 | 7.5 |
| 4 | 5 | 5 | 5 | 5 | 5 | 5 | 5 | 5 | 5 | 5 | 5 |
| 5 | 2 | 2 | 2 | 2 | 2 | 2 | 2 | 2 | 2 | 2 | 2 |
| 6 | 2.5 | 2.5 | 2.5 | 2.5 | 2.5 | 2.5 | 2.5 | 2.5 | 2.5 | 2.5 | 2.5 |
| 7 | 7 | 7 | 7 | 7 | 7 | 7 | 7 | 7 | 7 | 7 | 7 |
| 8 | 5 | 5 | 5 | 5 | 5 | 5 | 5 | 5 | 5 | 5 | 5 |
| 9 | 5 | 5 | 5 | 5 | 5 | 5 | 5 | 5 | 5 | 5 | 5 |
| 10 | 2 | 2 | 2 | 2 | 2 | 2 | 2 | 2 | 2 | 2 | 2 |
| 11 | 0 | 0 | 0.2 | 0 | 0.4 | 0.4 | 0.5 | 0.9 | 0.7 | 2.9 | 4.9 |
| 12 | 0 | 0.1 | 0.1 | 0.3 | 0.1 | 0 | 0 | 0.1 | 0.3 | 0.1 | 0.1 |
| 13 | 0 | 0 | 0 | 0 | 0 | 0.1 | 0 | 0 | 0 | 0 | 0 |
| 14 | 0 | Suitable amount | Suitable amount | Suitable amount | Suitable amount | Suitable amount | Suitable amount | Suitable amount | Suitable amount | Suitable amount | Suitable amount |
| 15 | 25 | 25 | 25 | 25 | 25 | 25 | 25 | 25 | 25 | 25 | 25 |
| 16 | 5 | 5 | 5 | 5 | 5 | 5 | 5 | 5 | 5 | 5 | 5 |
| Electrolyte concentration | 0 | 0.1 | 0.3 | 0.3 | 0.5 | 0.5 | 0.5 | 1 | 1 | 3 | 5 |
| Before incubation | + | + | + | + | + | + | + | + | + | + | + |
| 60° C., 4 days | − | − | − | − | + | + | + | + | + | + | + |
| 60° C., 7 days | − | − | − | − | + | + | + | + | + | + | + |

FORMULATION EXAMPLES

Based on the results obtained in Test Examples 1 to 4, sunscreen compositions were prepared as follows. The unit in each Formulation Example is wt. %. All of the following combinations show high SPF values and high PFA values; therefore, it can be determined that the desired effect can be obtained.

Formulation Example 1

Cyclopentasiloxane: 20
Hydrogenated polyisobutene: 5
Alkyl benzoate: 7
Caprylyl methicone: 3
Ethylhexyl methoxycinnamate: 7.5
Octocrylene: 3
Diethylamino hydroxybenzoyl hexyl benzoate: 3
Polysilicone-15: 3.5
Lauryl PEG-9 polydimethylsiloxyethyl dimethicone: 2.5
(Vinyl dimethicone/methicone silsesquioxane) crosspolymer (average particle diameter: 5 μm): 5
Polymethylsilsesquioxane: 5
Ethanol: 7.5
Antioxidant: suitable amount
Phenoxyethanol: 0.2
1,2-Pentanediol: 3
Disodium adenosine monophosphate: 0.5
Dipotassium glycyrrhizate: 0.1
Sodium chloride: 0.5
Citric acid: suitable amount
Water: 23
Total: 100

Formulation Example 2

Cyclopentasiloxane: 25
Alkyl benzoate: 5
Pentaerythrityl tetraethylhexanoate: 3
Ethylhexyl methoxycinnamate: 7.5
Octocrylene: 3
Diethylamino hydroxybenzoyl hexyl benzoate: 3
Polysilicone-15: 3.5
Phenylbenzimidazole sulfonic acid: 1
PEG-10 dimethicone: 3
(Vinyl dimethicone/methicone silsesquioxane) crosspolymer (average particle diameter: 5 μm): 4.5
Polymethylsilsesquioxane: 4
Trimethylsiloxysilicate: 1
Ethanol: 6
Antioxidant: suitable amount
Phenoxyethanol: 0.2
1,2-Pentanediol: 2
Adenosine monophosphate: 0.5
Stearyl glycyrrhetinate: 0.05
Triethanolamine: suitable amount
Water: 27
Total: 100

Formulation Example 3

Cyclopentasiloxane: 12
Hydrogenated polyisobutene: 15
Alkyl benzoate: 4
Erythrityl triethylhexanoate: 4
Ethylhexyl methoxycinnamate: 7.5
Octocrylene: 5
Diethylamino hydroxybenzoyl hexyl benzoate: 2
Bis-ethylhexyloxyphenol methoxyphenyl triazine: 1
Stearoyl inulin: 0.5
Lauryl PEG-9 polydimethylsiloxyethyl dimethicone: 1.7
PEG-30 dipolyhydroxystearate: 0.5
(Vinyl dimethicone/methicone silsesquioxane) crosspolyrner (average particle diameter: 5 μm): 4.5
Polymethylsilsesquioxane: 5
Trimethylsiloxysilicate: 1
Ethanol: 7
Antioxidant: suitable amount
Phenoxyethanol: 0.2

1,2-Pentanediol: 2
Adenosine monophosphate: 0.1
Sodium chloride: 0.5
Dipotassium glycyrrhizate: 0.03
Stearyl glycyrrhetinate: 0.03
Aminomethyl propanediol: suitable amount
Water: 26
Total: 100

Formulation Example 4

Cyclopentasiloxane: 20
Hydrogenated polyisobutene: 5
Alkyl benzoate: 8
Caprylyl methicone: 3
Ethylhexyl methoxycinnamate: 7.5
Octocrylene: 3
Diethylamino hydroxybenzoyl hexyl benzoate: 3
Polysilicone-15: 3.5
Lauryl PEG-9 polydimethylsiloxyethyl dimethicone: 2.5
PEG-30 dipolyhydroxystearate: 0.3
(Vinyl dimethicone/methicone silsesquioxane) crosspolymer
(average particle diameter: 5 μm): 5
Polymethylsilsesquioxane: 5
Ethanol: 7.5
Antioxidant: suitable amount
Phenoxyethanol: 0.2
1,2-Pentanediol: 3
Adenosine monophosphate: 0.5
Sodium chloride: 0.5
Aminomethyl propanediol: suitable amount
Water: 27
Total: 100

Formulation Example 5

Cyclopentasiloxane: 25
Alkyl benzoate: 5
Pentaerythrityl tetraethylhexanoate: 3
Ethylhexyl methoxycinnamate: 7.5
Octocrylene: 3
Diethylamino hydroxybenzoyl hexyl benzoate: 3
Polysilicone-15: 3.5
Phenylbenzimidazole sulfonic acid: 1
Lauryl PEG-9 polydimethylsiloxyethyl dimethicone: 2
PEG-30 dipolyhydroxystearate: 0.5
(Vinyl dimethicone/methicone silsesquioxane) crosspolymer
(average particle diameter: 5 μm): 4.5
Polymethylsilsesquioxane: 4
Trimethoxysilicate: 1
Ethanol: 7.5
Antioxidant: suitable amount
Phenoxyethanol: 0.2
1,2-Pentanediol: 2
Adenosine monophosphate: 0.5
Triethanolamine: suitable amount
Water: 27
Total: 100

Formulation Example 6

Cyclopentasiloxane: 25
Caprylyl methicone: 3
Alkyl benzoate: 5
Ethylhexyl methoxycinnamate: 10
Diethylamino hydroxybenzoyl hexyl benzoate: 3
Hydrophobized particulate titanium oxide: 3
Hydrophobized particulate zinc oxide: 3
(Vinyl dimethicone/methicone silsesquioxane) crosspolymer (average particle diameter: 5 μm): 4
PEG-9 polydimethylsiloxyethyl dimethicone: 3
Trimethylsiloxysilicate: 1
Glycerol: 2
Ethanol: 8
Phenoxyethanol: 0.2
1,2-Pentanediol: 1
Glycerol: 1
Sodium chloride: 0.5
Antioxidant: suitable amount
Water: 27
Total: 100

Formulation Example 7

Cyclopentasiloxane: 10
Hydrogenated polyisobutene: 15
Alkyl benzoate: 5
Erythrityl triethylhexanoate: 4
Ethylhexyl methoxycinnamate: 7
Octocrylene: 4
Diethylamino hydroxybenzoyl hexyl benzoate: 3
Polysilicone-15: 3
Stearoyl inulin: 0.5
Highly polymerized dimethicone: 0.2
Lauryl PEG-9 polydimethylsiloxyethyl dimethicone: 1.7
PEG-30 dipolyhydroxystearate: 0.5
(Vinyl dimethicone/methicone silsesquioxane) crosspolymer
(average particle diameter: 5 μm): 4.5
Polymethylsilsesquioxane: 3
Trimethoxysilicate: 1
Ethanol: 7
Antioxidant: suitable amount
Phenoxyethanol: 0.2
1,2-Pentanediol: 2
Adenosine monophosphate: 0.1
Magnesium ascorbyl phosphate: 1
Aminomethyl propanediol: suitable amount
Water: 26
Total: 100

Formulation Example 8

Cyclopentasiloxane: 20
Dimethicone: 5
Alkyl benzoate: 5
Erythrityl triethylhexanoate: 4
Ethylhexyl methoxycinnamate: 7.5
Diethylamino hydroxybenzoyl hexyl benzoate: 3
Polysilicone-15: 5
Lauryl PEG-9 polydimethylsiloxyethyl dimethicone: 1.7
PEG-30 dipolyhydroxystearate: 0.4
(Vinyl dimethicone/methicone silsesquioxane) crosspolymer
(average particle diameter: 5 μm): 4.5
Polymethylsilsesquioxane: 3
Ethanol: 6
Antioxidant: suitable amount
Phenoxyethanol: 0.1
1,2-pentanediol: 1
Glycerol: 2
Menthol: 0.2

Essential oil: 0.1
(star anise oil, *Pinus sylvestris* oil, *Lavandula hybrida* oil)
Adenosine monophosphate: 1
Aminomethyl propanediol: suitable amount
Water: 30
Total: 100

Formulation Example 9

Cyclopentasiloxane: 15
Hydrogenated polyisobutene: 15
Ethanol: 8
Ethylhexyl methoxycinnamate: 8
$C_{12-15}$ Alkyl benzoate: 6
Polymethylsilsesquioxane: 5
(Vinyl dimethicone/methicone silsesquioxane) crosspolymer
(average particle diameter: 5 μm): 5
Diethylamino hydroxybenzoyl hexyl benzoate: 3
Polysilicone-15: 3
Glycerol: 3
Lauryl PEG-9 polydimethylsiloxyethyl dimethicone: 2.5
Sodium chloride: 1
Adenosine monophosphate: 0.5
*Artemisia capillaris* extract: suitable amount
Clove extract: suitable amount
Aminomethyl propanediol: suitable amount
1,3-Butylene glycol: suitable amount
Glycerol fatty acid ester: suitable amount
Antioxidant: suitable amount
Water: 23
Total: 100

The invention claimed is:

1. A sunscreen composition free from a metal oxide comprising three or more oil-soluble ultraviolet absorbers, composite silicone particles having an average particle diameter of 10 μm or less, and an electrolyte, wherein:
the oil-soluble ultraviolet absorbers are at least three members selected from the group consisting of ethylhexyl methoxycinnamate, octocrylene, diethylamino hydroxybenzoyl hexyl benzoate, and polysilicone-15,
the composite silicone particles are composite silicone particles in which silicone rubber is coated with a silicone resin, and
the electrolyte is at least one electrolyte selected from the group consisting of sodium chloride, magnesium chloride, calcium chloride, adenosine phosphate and salts thereof, ascorbic acid and salts thereof, glucoside ascorbate and salts thereof, and sodium ascorbyl phosphate,
the oil-soluble ultraviolet absorbers are contained in an amount of 10 to 25 wt. %,
the composite silicone particles are contained in an amount of 4 to 20 wt. %,
the electrolyte is contained in an amount of 0.5 to 5 wt. %,
the sunscreen composition is in the form of a water-in-oil type (W/O) emulsion, and
the sunscreen composition is in a reversible separation state which is separated into two layers when allowed to stand and returns to a homogeneous single-layer emulsion form by shaking.

2. The sunscreen composition according to claim 1, comprising ethylhexyl methoxycinnamate, octocrylene, diethylamino hydroxybenzoyl hexyl benzoate, and polysilicone-15.

3. The sunscreen composition according to claim 1, wherein the composite silicone particles are composite silicone particles in which spherical silicone rubber is coated with a silicone resin.

4. The sunscreen composition according to claim 1, wherein 10 to 40 wt. % of water is contained in the sunscreen composition.

* * * * *